(12) United States Patent
Suzuki et al.

(10) Patent No.: US 7,521,109 B2
(45) Date of Patent: Apr. 21, 2009

(54) ABSORBER INCLUDING BY-PASS CHANNEL MEMBER AND ABSORBER PRODUCT THEREFROM

(75) Inventors: Migaku Suzuki, Kanagawa (JP); Reiko Moriya, Kanagawa (JP)

(73) Assignee: Japan Absorbent Technology Institute, Tokyo (JP)

( * ) Notice: Subject to any disclaimer, the term of this patent is extended or adjusted under 35 U.S.C. 154(b) by 338 days.

(21) Appl. No.: 10/509,865

(22) PCT Filed: Apr. 4, 2003

(86) PCT No.: PCT/JP03/04342

§ 371 (c)(1),
(2), (4) Date: Oct. 1, 2004

(87) PCT Pub. No.: WO03/084452

PCT Pub. Date: Oct. 16, 2003

(65) Prior Publication Data

US 2005/0147810 A1   Jul. 7, 2005

(30) Foreign Application Priority Data

Apr. 5, 2002   (JP) .............................. 2002-103743

(51) Int. Cl.
  *B32B 3/10*   (2006.01)
  *A61F 13/15*   (2006.01)

(52) U.S. Cl. .................. 428/137; 428/138; 604/385.01; 604/385.101

(58) Field of Classification Search ................. 428/166, 428/137, 138, 172; 604/385.01, 385.101

See application file for complete search history.

(56) References Cited

U.S. PATENT DOCUMENTS

| 3,122,142 | A | * | 2/1964 | Crowe, Jr. .................. 604/369 |
| 4,323,069 | A | * | 4/1982 | Ahr et al. .................... 604/378 |
| 4,731,071 | A | * | 3/1988 | Pigneul ................. 604/385.23 |
| 5,334,289 | A | * | 8/1994 | Trokhan et al. .......... 162/358.2 |
| 5,947,945 | A | * | 9/1999 | Cree et al. .................. 604/368 |
| 6,984,225 | B2 | | 1/2006 | Raidel et al. |

FOREIGN PATENT DOCUMENTS

| CN | 1213288 A | 4/1999 |
| JP | U 55-56625 | 4/1980 |
| JP | A 63-256701 | 10/1988 |
| JP | U 6-58931 | 8/1994 |
| JP | A 2000-201975 | 7/2000 |
| JP | A 2002-20957 | 1/2002 |
| JP | A 2003-103677 | 4/2003 |
| JP | A 2003-103740 | 4/2003 |
| WO | WO 01/24750 | * 4/2001 |

* cited by examiner

*Primary Examiner*—Donald Loney
(74) *Attorney, Agent, or Firm*—Oliff & Berridge, PLC

(57) ABSTRACT

An absorber comprising a laminate of two or more layers of highly water-absorbent sheets each containing a highly water-absorbent resin in high proportion, which absorber can satisfactorily cope with the feeding speed of aqueous liquid. In particular, an absorber comprising a laminate water-absorbent member, the laminate water-absorbent member consisting of a laminate of two or more layers of highly water-absorbent sheets each containing a highly water-absorbent resin and capable of absorbing an aqueous liquid, and a by-pass channel member, the by-pass channel member having a channel for, providing that an upper side refers to the side of laminate water-absorbent member fed with the aqueous liquid, moving the aqueous liquid fed to a first highly water-absorbent sheet disposed at the uppermost part of the laminate water-absorbent member from the first highly water-absorbent sheet to another highly water-absorbent sheet.

12 Claims, 9 Drawing Sheets

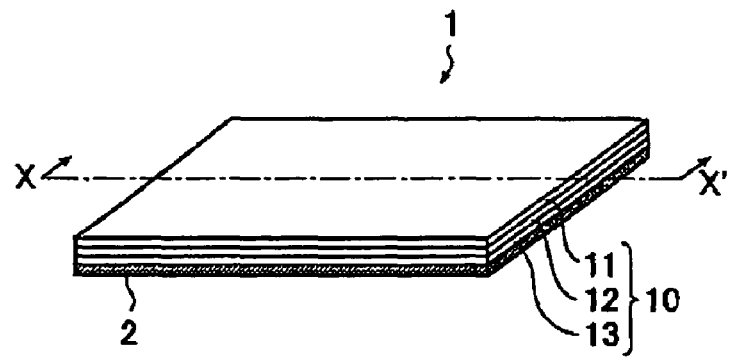
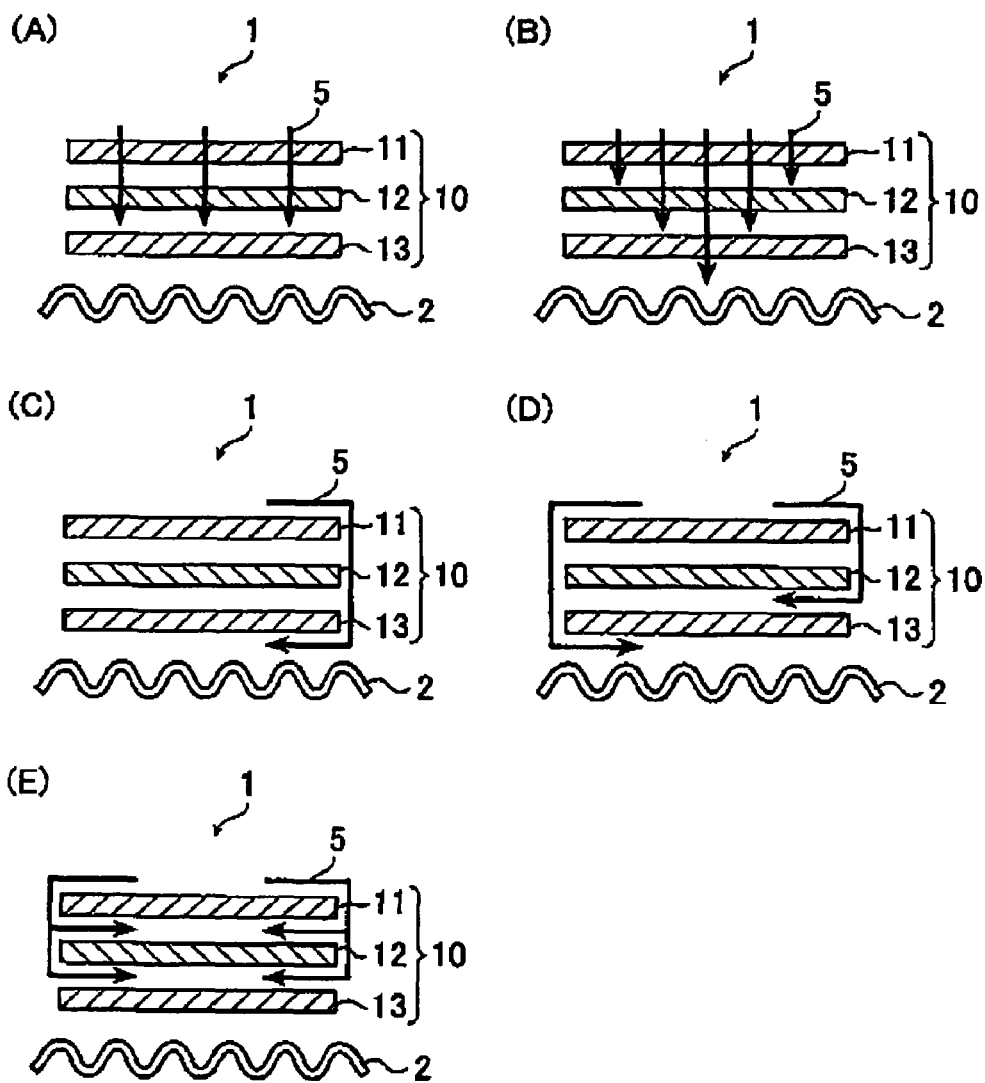

FIG. 4
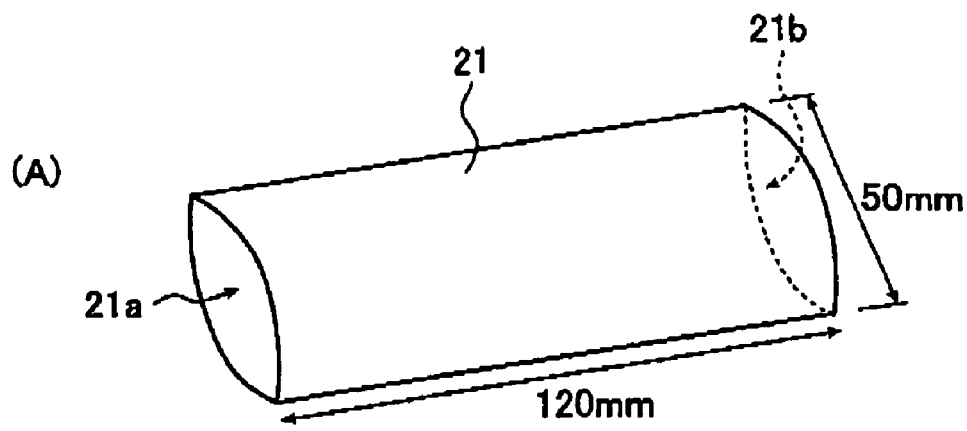
(A)
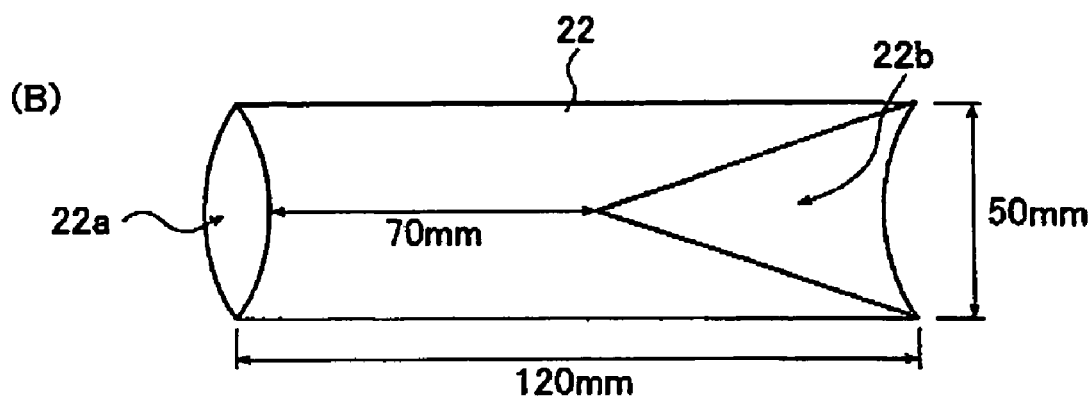
(B)
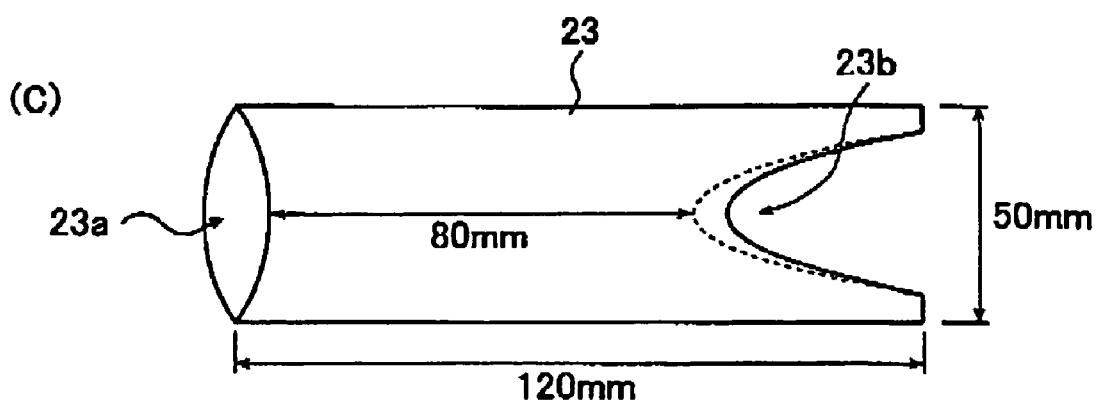
(C)

FIG. 5
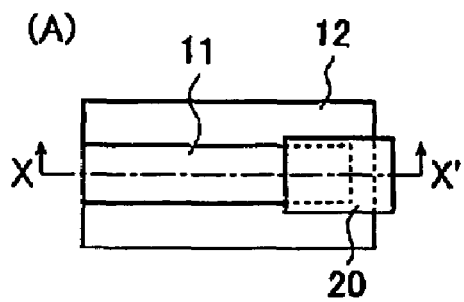
(A)
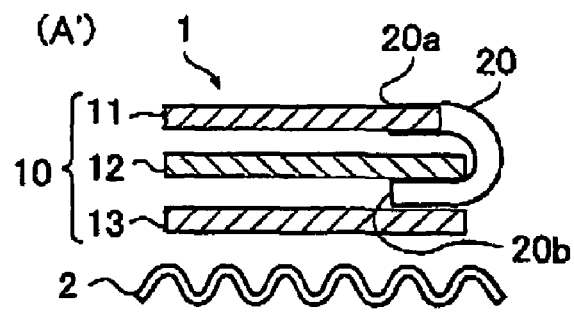
(A')
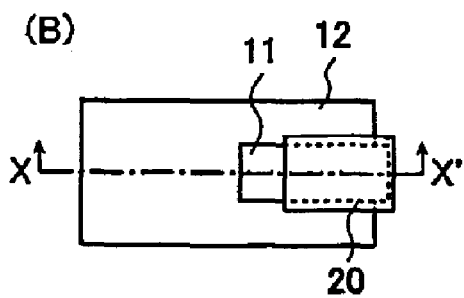
(B)
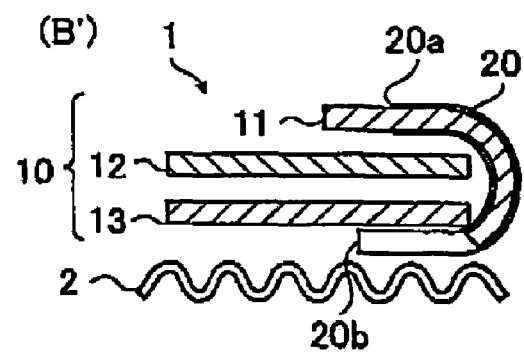
(B')
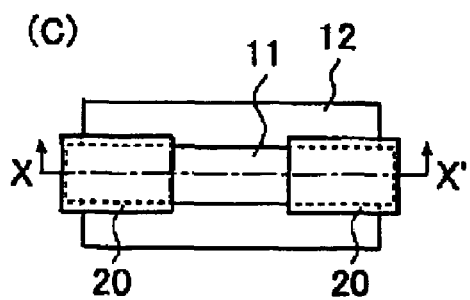
(C)
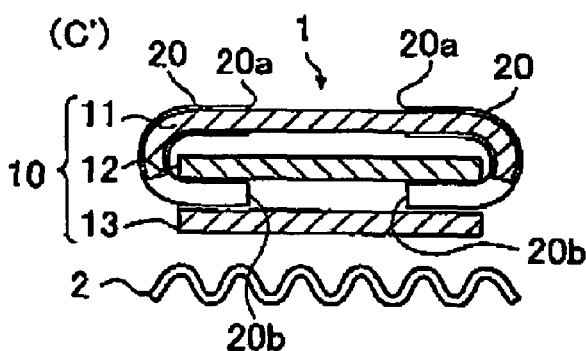
(C')
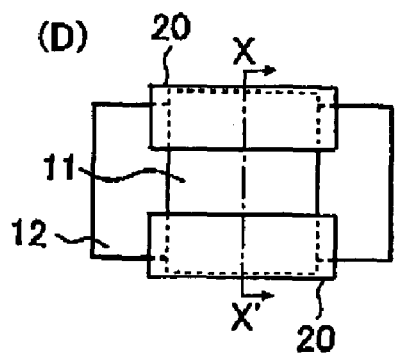
(D)
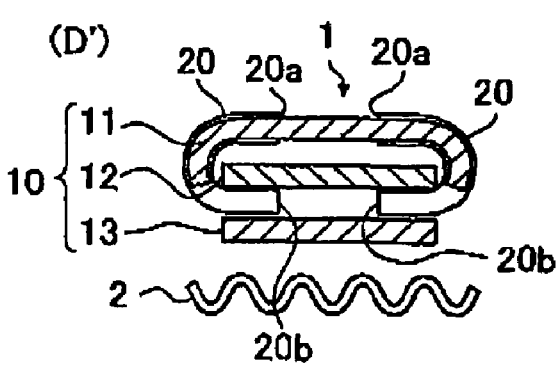
(D')

ABSORBER INCLUDING BY-PASS CHANNEL MEMBER AND ABSORBER PRODUCT THEREFROM

TECHNICAL FIELD

The present invention relates to an absorber which is applied to various absorbent products as an element constituting the main part of its absorptive function, more precisely, to an absorber which can quickly absorb aqueous liquid when a large amount of it is fed in a short period of time to the surface of the absorber as a result of excretion.

Furthermore, the present invention relates to absorbent products such as paper diapers, sanitary napkins, and incontinence products, using the absorber.

BACKGROUND ART

An absorbent product includes an absorber as its primary component. At present, in most of absorbent products available in the market, the absorber is structured as a single layer of a mixture made of super-absorbent polymer (also referred to as "SAP" hereinafter) and pulp. This single layer structure is sometimes formed with its components uniformly distributed in a single layer, but in general, it just has the appearance of being a single layer.

In other words, these absorbers, whose main component is pulp, are structured, in general, to have a gradient in a concentration distribution of the SAP and the pulp. Specifically, the single layer structure is formed of, most commonly, an upper layer primarily consisting of pulp, a middle layer primarily of SAP, and a bottom layer primarily of pulp, by compressing and bonding these three layers of different constitution from one another into one, and further by the so-called "core wrapping" process in which the above is wrapped with tissue and non-woven fabric, to prevent desorption and scattering of pulp and SAP.

Incidentally, in recent years, research and development in super-absorbent sheet containing fibrous and powder SAP in high proportion as a single-layer-structure absorber has been actively carried out.

For applications that do not require a great absorbing capacity, such as sanitary napkins, slight-incontinence products for women, etc., this super-absorbent sheet is most commonly used as a single layer rather than stacking the sheets to form multiple layers, but for applications that require a great absorbing capacity, such as baby diapers, adult incontinence diapers, etc., the super-absorbent sheets are generally laminated to make a double-layer or triple-layer to give the required absorbing capacity. Because this super-absorbent sheet is much thinner than the afore-mentioned conventional absorber whose main component is pulp, the super-absorbent sheet can be used in a laminate of multiple layers as described above. Moreover, it has an advantage of being far thinner, even when it is used as a laminated structure of multiple layers, than the conventional absorber whose main component is pulp.

In cases where the super-absorbent sheets are laminated to form multiple layers as mentioned above, if the afore-mentioned super-absorbent sheets are simply stacked to form the multiple-layer-structure, due to spaces between respective layers, aqueous liquid such as excreted urine that seeps into the first, or top, layer cannot be uniformly transferred to the second or further lower layers. As a result, it will be difficult to fully function as an absorber. These super-absorbent sheets, therefore, are used, in case these super-absorbent sheets are laminated to form multiple layers, by making them into one body using adhesive or other bonding material. Thus the extremely thin absorber with a great absorbing capacity potential can be obtained by laminating the super-absorbent sheets in multiple layers.

In real-life situations, however, the absorber which can be obtained by laminating the super-absorbent sheets in multiple layers has a disadvantage that its absorbing speed cannot keep up with the speed of the excreted liquid that flows into the absorber, which results in its leaking easily, without exerting its inherent absorbing capability.

According to the research by the inventors of the present invention, a limit of the speed of absorption by swelling of the SAP due to characteristics of the SAP and the aqueous liquid, and insufficient space for liquid retention due to the absorber's extreme thinness are cited as causes for the disadvantage described above. In addition to these, it has also been identified that the overall rate of utilization of the absorbent is lowered by SAP's tendency to cause blocking, on top of its slow absorbing speed, though its absorbing capacity is extremely high in comparison to the pulp, the main component of the conventional absorber, whose absorbing capacity is small though its absorbing speed is high.

Because in case two or more super-absorbent sheets are laminated, the above problem becomes even more evident, research for a method of making the aqueous liquid fed to the top super-absorbent sheet seep into other super-absorbent sheets quickly and uniformly have been conducted and a technique of inserting between respective layers highly hydrophilic non-woven fabrics as diffusion sheets, a technique of physically making large apertures or cutting slits and the like have been proposed, but so far no effective solution has been found. With this background, while an advent of absorbent products comprising the laminated super-absorbent sheets in multiple layers has been desired, it has not yet been realized so far.

DISCLOSURE OF THE INVENTION

An object of the present invention, therefore, is to provide an absorber which can satisfactorily cope with the feeding speed of aqueous liquid into the absorber, comprising two or more laminated super-absorbent sheets, each of which containing SAP in high content.

The inventors of the present invention have discovered that it is possible, by providing a by-pass channel member for by-passing from the uppermost surface layer to the lower layers in an absorber composed by laminating super-absorbent sheets in multiple layers, to realize an absorber that fully cope with the flow speed of the aqueous liquid into it and furthermore achieves a faster absorbing speed than that of the conventional thick absorber whose main component is pulp, and have completed the present invention.

In other words, the present invention provides the following (1) through (13).

(1) An absorber comprising a laminated absorbent member consisting of laminated two or more super-absorbent sheets, each of which containing super-absorbent polymers to be capable of absorbing aqueous liquid, and a by-pass channel member which has a channel for moving the aqueous liquid fed to a first super-absorbent sheet positioned uppermost in the laminated absorbent member from the first super-absorbent sheet to another super-absorbent sheet, wherein the side to be fed with the aqueous liquid in the laminated absorbent member is assumed to be an upper side.

The absorber of the present invention can achieve an extremely high absorbing speed by utilizing the absorbing capability of multiple layers, wherein an aqueous liquid fed to the first super-absorbent sheet of the laminated super-absorbent sheets in multiple layers, i.e., the super-absorbent sheet positioned closest to a wearer's side when it is worn by the wearer, is distributed to other layers via the by-pass channel member.

(2) The absorber described according to (1), wherein at least one layer of the super-absorbent sheets contains 50 wt % or more of the super-absorbent polymer and a thickness thereof is 1.5 mm or less.

(3) The absorber according to (1) or (2), wherein all of the super-absorbent sheets contain 50 wt % or more of the super-absorbent polymer and thicknesses thereof are 1.5 mm or less.

(4) The absorber according to any one of (1) to (3), wherein at least a part of the by-pass channel member is composed of a tube member that has a channel inside;

an entry end portion is formed by positioning one end of the tube member above the first super-absorbent sheet, or by positioning the end of the tube member such that an end portion of the first super-absorbent sheet is inserted in the channel; and an exit end portion is formed by positioning the other end of the tube member either above another super-absorbent sheet or under the laminated absorbent member or both, or by positioning the other end of the tube member such that at least one end of another super-absorbent sheet is inserted in the channel.

(5) The absorber according to (4), wherein water-transferring sheet is provided in the channel of the tube member.

(6) The absorber according to any one of (1) to (5), wherein at least a part of the by-pass channel member is composed of a concavity-and-convexity-containing sheet member that has a concavity-and-convexity-containing surface with concave portions and convex portions on at least one surfaces thereof;

a part of the concavity-and-convexity-containing sheet member is positioned above the first super-absorbent sheet with the concavity-and-convexity-containing surface facing upward; and another part of the concavity-and-convexity-containing sheet member is positioned either above another respective super-absorbent sheet or under the laminated absorbent member or both.

(7) The absorber according to (6), wherein the concavity-and-convexity-containing sheet member has apertures in some of or in all of the convex portions.

(8) The absorber according to any one of (1) to (7), wherein at least a part of the by-pass channel member is composed of a non-woven sheet member:

a part of the non-woven sheet member is positioned above the first super-absorbent sheet; and another part of the non-woven sheet member is positioned either above another super-absorbent sheet or under the laminated absorbent member or both.

(9) The absorber according to (8), wherein the part of the non-woven sheet member is positioned above the first super-absorbent sheet so as to rise from a surface thereof.

(10) The absorber according to (8), wherein the part of the non-woven sheet member covers an area in vicinity of a center portion of the first super-absorbent sheet, and functions as a skin-contact sheet.

(11) The absorber according to any one of (1) to (10), wherein at least a part of the by-pass channel member is composed of hydrophilic fiber or hydrophilic fiber bundle; and at least the first super-absorbent sheet and another super-absorbent sheet which makes contact therewith are sewn up with the hydrophilic fiber or hydrophilic fiber bundle.

(12) The absorber according to (11), wherein a permeable fiber web is provided above the first super-absorbent sheet; and at least the permeable fiber web, the first super-absorbent sheet and said another super-absorbent sheet which makes contact therewith are sewn up by a needle-punching process.

(13) An absorbent product used to be fed with an aqueous liquid from an upper side thereof, comprising an aqueous liquid permeable sheet member, the absorber according to any one of (1) to (12), and an aqueous liquid impermeable sheet member, from the top in this order.

BRIEF DESCRIPTION OF THE DRAWINGS

FIG. 2 is an illustration showing an example of the absorber of the present invention.

FIG. 3 is a group of conceptual diagrams explaining the movement of the aqueous liquid caused by the channels of the by-pass channel member in the absorber of the present invention. FIGS. 3(A) through (E) are sectional views of the example shown in FIG. 2, taken along the line X to X'.

FIGS. 4(A) through (C) are the illustrative perspective views of the examples of the tube member, each having a channel inside.

FIG. 5 is a group of explanatory drawings showing examples of the tube member disposition. FIGS. 5(A) through (D) are the top views and FIGS. 5(A') through (D') are the sectional views taken along the line X to X' of each.

FIGS. 8(A) through (D) are the sectional views of the examples of the absorber of the present invention.

FIG. 10(A) is a top view and FIG. 10(B) is a sectional view taken along the line X to X' of FIG. 10(A).

BEST MODE FOR CARRYING OUT THE INVENTION

Hereinafter, the absorber and the absorbent products of the present invention will be described in detail in accordance with preferred embodiments shown in accompanying drawings.

First, the principle of the present invention will be explained. The principle of the present invention can be explained by making an analogy to an irrigation system that transfers irrigation water effectively and quickly to rice paddies.

Figure 1:
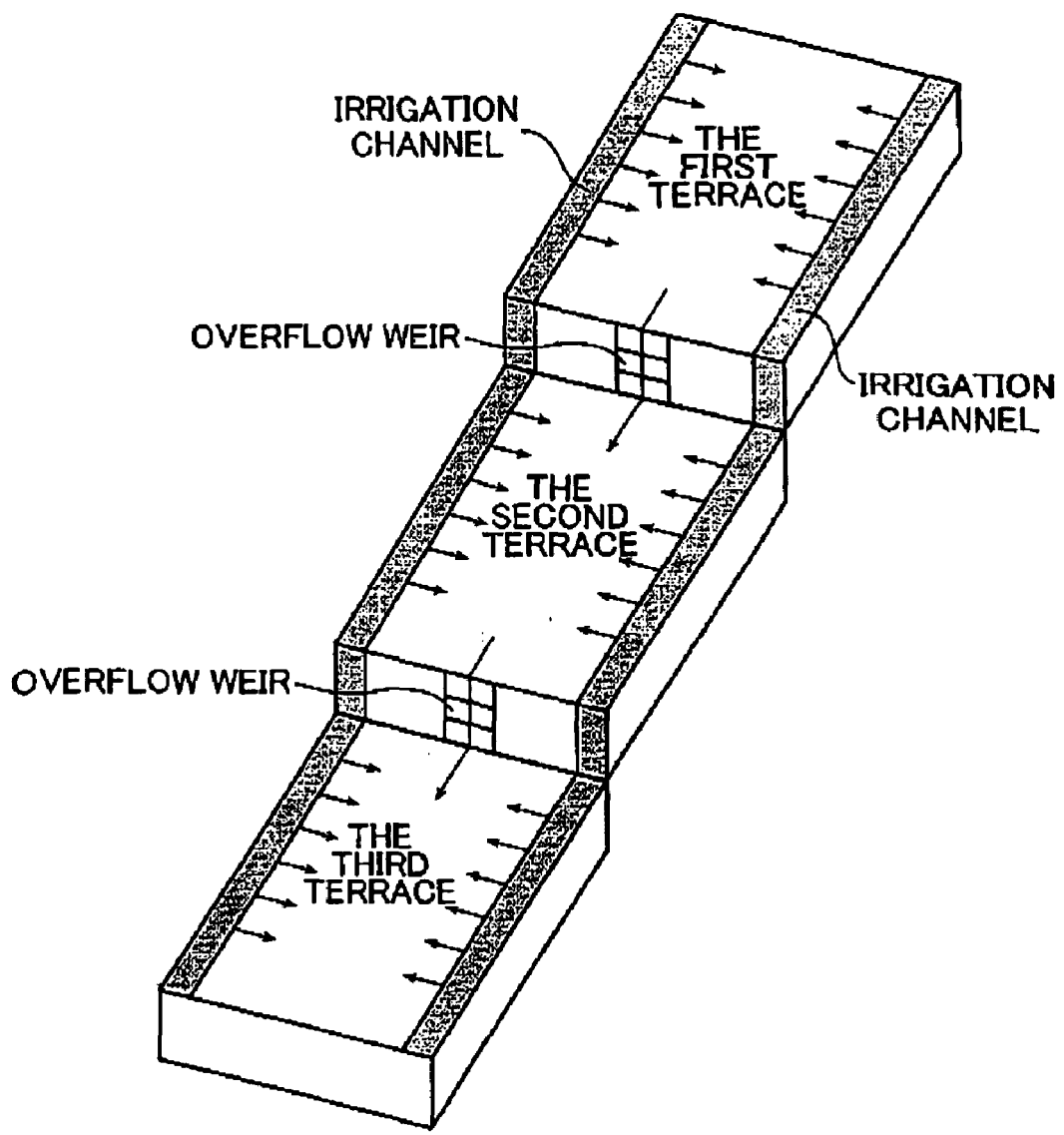
FIG. 1 is an illustration of an irrigation system, explaining the principle of the present invention.

FIG. 1 is an illustration of an irrigation system, explaining the principle of the present invention. The design concept of a conventional absorber obtained by laminating super-absorbent sheets in multiple layers, when likened to an irrigation system that supplies irrigation water to 3-terraced rice paddies the first, second and the third terrace, is to supply irrigation water to fill rice paddies on the first terrace, then let the water spill over the overflow weir and flow into rice paddies on the second terrace to fill the rice paddies on the second terrace, and further let the water spill over the overflow weir and flow into rice paddies on the third terrace. That is, it takes time to supply irrigation water.

In contrast to this, the design concept of the absorber of the present invention serves, as shown in FIG. 1, to provide irrigation channels capable of supplying irrigation water from the rice paddies on the first terrace to other rice paddies. This allows supplying of the irrigation water via irrigation channels to the second and the third terrace almost simultaneously with supplying the irrigation water to the first terrace, and thus filling of all the rice paddies with irrigation water in a short period of time. In the absorber of the present invention, the role of the above irrigation channels is taken by the by-pass channel member which will be discussed later.

FIG. 2 is an illustration showing an example of the absorber of the present invention.

The absorber 1 of the present invention includes a laminated absorbent member 10 and a by-pass channel member. Note that the by-pass channel member is not shown in FIG. 2.

Although the laminated absorbent member 10 in FIG. 2. is composed of three layers of laminated super-absorbent sheets 11, 12, and 13, there is no particular limit to the number of layers to laminate as long as 2 or more layers are made.

The super-absorbent sheet used in the present invention is an absorber in extremely thin sheet form whose primary constituent is SAP. It is preferred that the SAP content of the super-absorbent sheet is 50 wt % or more, and more preferably 60 to 95 wt %. Because the SAP content is extremely high as indicated above, the super-absorbent sheet used in the present invention is extremely thin. It is preferred that the thickness of the super-absorbent sheet is 1.5 mm or less, and more preferably 1 mm or less.

There is no limit in particular to the structure or the manufacturing method of the super-absorbent sheet used in the present invention, as long as it is an absorber in extremely thin sheet form with its primary constituent being SAP.

For example, there is a super-absorbent sheet obtained by the Air Laid method. The Air Laid method is a method for obtaining a super-absorbent sheet by mixing pulverized pulp and SAP, adding a binding agent to the mixture, and shaping it into a sheet form. NovaThin (U.S. Registered Trademark), manufactured by Rayonier Inc. in the U.S., and KIN-OCLOTH (Registered Trademark), manufactured by Oji Kinocloth Co., Ltd., for example, are known as super-absorbent sheets obtained by this method.

There is also a super-absorbent sheet obtained by the method of coating an aqueous liquid permeable sheet such as non-woven fabric with a SAP dispersion slurry. The SAP dispersion slurry here is preferred to be a slurry obtained by dispersing SAP and Micro Fibrillated Cellulose (MFC) in a mixed solvent of water and ethanol. MegaThin (Registered Trademark), manufactured by Japan Absorbent Technology Institute, for example, is known as a super-absorbent sheet obtained by this method.

There are also other examples such as a super-absorbent sheet obtained by the method of applying a large amount of SAP which is supported by raised non-woven fabric, and settling it with a hot-melt binder, emulsion binder, water-soluble fiber, etc., as well as a super-absorbent sheet obtained by the method of mixing fibrous SAP and PET (polyethylene terephthalate) fiber, and forming the mixture into a web.

The absorber of the present invention is characterized by comprising, in addition to the afore-mentioned laminated absorbent member, a by-pass channel member which has a channel for moving the aqueous liquid (urine, for example) fed to the first super-absorbent sheet 11 which is positioned at the uppermost part of the laminated absorbent member, from the first super-absorbent sheet 11 to another super-absorbent sheet (super-absorbent sheets 12 and 13 in FIG. 2). Note that in the present specification, the side where the aqueous liquid is fed is referred to as the "upper" side and the opposite side is referred to as the "bottom" side of the laminated absorbent member. More specifically, the side closer to a user's skin is referred to as the "upper" side and the side away from the skin is referred to as the "bottom" side when the user actually wears the absorbent product of the present invention using the absorber of the present invention.

There is no limit in particular to the shape, size, material, disposition, etc. of the by-pass channel member used in the present invention, as long as it has a channel to move the aqueous liquid from the first super-absorbent sheet 11 to the other super-absorbent sheets 12 and 13.

First, the function of the by-pass channel member will be explained.

FIG. 3 is a group of conceptual diagrams explaining the movement of the aqueous liquid caused by the channel of the by-pass channel member in the absorber of the present invention. FIGS. 3(A) through (E) are sectional views of the example shown in FIG. 2, taken along the line X to X'. Note that the present invention shall not be limited by these.

In the example shown in FIG. 3(A), a by-pass channel member is provided to move the aqueous liquid 5 fed to the first super-absorbent sheet 11, from the first super-absorbent sheet 11 to the top of another super-absorbent sheet 13.

In the example shown in FIG. 3(B), a by-pass channel member is provided to move the aqueous liquid 5 fed to the first super-absorbent sheet 11, from the first super-absorbent sheet 11 downward beneath another super-absorbent sheet 13 (that is, between the super-absorbent sheet 13 and the back-sheet 2) in the center area in the X-X' direction, to the top of the super-absorbent sheet 13 on both sides adjacent to this center area, and to the top of the super-absorbent sheet 12 on both further sides of the above.

In the example shown in FIG. 3(C), a by-pass channel member is provided to move the aqueous liquid 5 fed to the first super-absorbent sheet 11, from the first super-absorbent sheet 11 downward beneath the super-absorbent sheet 13. Furthermore, a by-pass channel member is provided to circumvent the ends of the super-absorbent sheets 11, 12 and 13.

In the example shown in FIG. 3(D), a by-pass channel member is provided to move the aqueous liquid 5 fed to the first super-absorbent sheet 11, from the first super-absorbent sheet 11 downward beneath the super-absorbent sheet 13 at the left end of the absorber 1 as shown in FIG. 3(D), and from the first super-absorbent sheet 11 to the top of the super-absorbent sheet 13 at the right end of the absorber 1. Furthermore, a by-pass channel member is provided to circumvent the ends of the super-absorbent sheets 11, 12 and 13.

In the example shown in FIG. 3(E), a by-pass channel member is provided to move the aqueous liquid 5 fed to the first super-absorbent sheet 11, from the first super-absorbent sheet 11 to the top of the super-absorbent sheet 12 and to the top of the super-absorbent sheet 13, respectively. Furthermore, a by-pass channel member is provided to circumvent the ends of the super-absorbent sheets 11 and 12.

The disposition of the by-pass channel member can be determined according to such conditions as the shape, material, and characteristics thereof.

As described above, movement and introduction of the aqueous liquid between the layers is carried out effectively by the by-pass channel member. In other words, a large amount of the aqueous liquid such as urine fed in a short period of time to the surface of the first super-absorbent sheet 11, can be moved rapidly to the other super-absorbent sheet(s) 12 and/or 13.

As long as it has a channel to move the aqueous liquid from the first super-absorbent sheet 11 to other super-absorbent sheets 12 and 13, there is no particular limit to the by-pass channel member used in the present invention, as mentioned above, but the followings may be preferably used: (1) a tube member that has a channel inside, (2) a concavity-and-convexity-containing sheet member that has at least one concavity-and-convexity-containing surface having concave portions and convex portions (hereinafter referred to simply as "concavity-and-convexity-containing sheet member"), (3) a non-woven sheet member, and (4) hydrophilic fiber or its fiber bundle. One of these is used alone or two or more of these are used in combination.

Hereinafter, the above (1) through (4) listed as preferred by-pass channel members will be explained.

(1) Tube Member that has a Channel Inside.

There is no particular limit to the shape, size, material, manufacturing method, etc. of the tube member with a channel inside of it. FIGS. 4(A) through (C) are the illustrative perspective views of the examples of the tube member, each having a channel inside. These tube members may be obtained by, for example, forming a flat tube using film.

In the tube member 21 shown in FIG. 4(A), the entry end portion 21a and the exit end portion 21b are of the same shape, and the length stays same along the line of channel.

In the tube member 22 shown in FIG. 4(B), the entry end 22a is of the same shape as that of FIG. 4(A), but the exit end portion 22b has a triangular notch on one side. Therefore, when the exit end portion 22b is positioned such that the side with the triangular notch faces upward, the aqueous liquid is quickly distributed to the super-absorbent sheet located above the exit end portion 22b, and when the exit end portion 22b is positioned such that the side with the triangular notch faces downward, the aqueous liquid is quickly distributed to the super-absorbent sheet positioned under the exit end portion 22b.

In the tube member 23 shown in FIG. 4(C), the entry end portion 23a is of the same shape as that of FIG. 4(A), but the exit end portion 23b has an almost semicircle notch on both sides. Therefore, in the portion where the tube length along the line of the channel is shortest due to these notches of the exit end portion 23b, the aqueous liquid is distributed quickly to the super-absorbent sheets.

There is no limit in particular to the size of the tube member. Although an example of the size of the tube member is shown in FIGS. 4(A) through (C), the present invention shall not be limited by this.

As the material for the tube member, followings can be exemplified: an aqueous liquid impermeable film made of resin such as PE (polyethylene), PP (polypropylene), PVA (polyvinyl alcohol), and urethane; and a water-resistant non-woven fabric such as SMS non-woven fabric (of three-layer structure of spunbond/meltblown/spunbond), and SMMS non-woven fabric (non-woven fabric of four-layer structure of spunbond/meltblown/meltblown/spunbond).

As the tube member, a tube in a form similar to what is obtained by cutting the bottom of a PE bag of 50 to 100 mm in width, 100 to 200 mm in length and 5 to 20 μm in thickness for household use; or a tube obtained by cutting a tube similar to a rain-drop protection PE tube for wet umbrellas to the appropriate length, for example, can be used.

Next, the disposition of the tube member is explained.

FIG. 5 is a group of explanatory drawings showing examples of the tube member disposition. In FIG. 5, the absorber 1 of the present invention has a laminated absorbent member 10 composed of three layers of super-absorbent sheets 11, 12, and 13, a tube member 20, and a back-sheet 2 provided under a super-absorbent sheet 13. FIGS. 5(A) through (D) are the top views and FIGS. 5(A') through (D') are the sectional views taken along the line X to X' of each.

One end of the tube member is positioned above the first super-absorbent sheet or is placed in such a way that the end portion of the first super-absorbent sheet is inserted into the channel of the tube member, to thereby form an entry end portion.

In each example shown in FIGS. 5(A') through (D'), one end of the tube member 20 is positioned in such a way that the end portion of the first super-absorbent sheet 11 is inserted into the channel of the tube member, to form the entry end portion 20a. The present invention, however, shall not be limited by this, and one end of the tube member may also be placed above the first super-absorbent sheet to form the entry end portion.

Furthermore, the other end of the tube member is positioned either above another super-absorbent sheet or under the laminated absorbent member or both, or is positioned in such a way that at least one of the end portions of another super-absorbent sheet is inserted into the channel of the tube member, to form an exit end portion.

In each example shown in FIGS. 5(A'), (C'), and (D'), the other end of the tube member 20 is positioned above the super-absorbent sheet 13 (that is, between the super-absorbent sheet 12 and the super-absorbent sheet 13), to form the exit end portion 20b. Further, in the example shown in FIG. 5(B'), the other end of the tube member 20 is positioned under the laminated absorbent member 10 (that is, between the super-absorbent sheet 13 which is the lowermost layer of the laminated absorbent member 10 and the back-sheet 2), to form the exit end portion 20b. The present invention, however, shall not be limited by this, and the exit end portion may also be formed such that at least one of the ends of another super-absorbent sheet is inserted into the channel of the tube member.

In each example shown in FIGS. 5(A) through (D), an exposed portion of the first super-absorbent sheet 11 (a portion that is not inserted into the channel of the tube member 20) is small in comparison with the size of the surface of the super-absorbent sheet 12. Accordingly, while the major part of the fed aqueous liquid flows into the channel via this first super-absorbent sheet 11 being partially absorbed thereinto, the aqueous liquid which overflows from the first super-absorbent sheet 11 sideward moves directly to not through the channel, and then is absorbed by the second super-absorbent sheet 12.

In the example shown in FIG. 5(A), the first super-absorbent sheet 11 covers the super-absorbent sheet 12 fully in the length along the line of X-X'.

In the example shown in FIG. 5(B), while the end portion of the first super-absorbent sheet 11 is deeply inserted into the tube exceeding the bent section of the tube member 20, the super-absorbent sheet 12 is exposed when viewed from above the absorber 1.

In the example shown in FIG. 5(C), two tube members 20 are provided and the end portions of the first super-absorbent sheet 11 are deeply inserted into the tubes exceeding the bent sections of respective tube members 20, but because the super-absorbent sheet 11 is longer than the super-absorbent sheet 12, it covers the super-absorbent sheet 12 fully in the length along the line of X-X'.

The example shown in FIG. 5(D) represents the reversed vertical-to-horizontal positional relationship of the example shown in FIG. 5(C).

It is preferred that the tube members 20 are positioned so as to go around the end portions of the super-absorbent sheets as shown in each example in FIG. 5.

In each example shown in FIG. 5, as described above, the end portion of the super-absorbent sheet 11 is inserted into the channel of the tube member 20. This leads to a preferable result in which the distribution efficiency of the aqueous liquid is improved because the liquid is introduced to the channel. This leads to another preferable result in which disruption of the flow of the aqueous liquid due to deformation of the tube member 20 during use is prevented.

Note that in case the end portion of the super-absorbent sheet 11 is inserted into the channel of the tube member 20, the end portion may be inserted straightforward or inserted while being bent.

In the absorber of the present invention, it is also acceptable to separately provide a water-transferring sheet to conduct the aqueous liquid to the channel. The water-transferring sheet is a sheet that has the characteristics of enabling the transferring of the aqueous liquid (water-transferability) by using capillary action, and woven fabric or non-woven fabric can be used for it.

(2) Concavity-and-convexity-containing Sheet Member

In the concavity-and-convexity-containing sheet member that has at least one concavity-and-convexity-containing surface with concave portions and convex portions, a number of concave portions in a series function as the channel for the aqueous liquid. There is no limit in particular to the concavity-and-convexity-containing sheet member's shape, size, material, manufacturing method, etc., as long as it has at least one concavity-and-convexity-containing surface with concave portions and convex portions.

Figure 6:
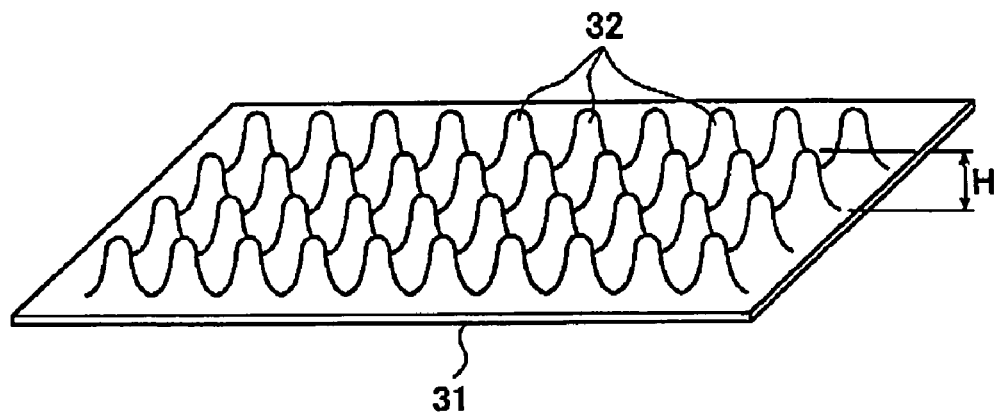
FIG. 6 is an illustrative perspective view of an example of the concavity-and-convexity-containing sheet member.

FIG. 6 is an illustrative perspective view of an example of the concavity-and-convexity-containing sheet member. The concavity-and-convexity-containing sheet member 31 shown in FIG. 6 has a number of projections 32 that form the convex portions.

As to the size of the concavity and convexity of the concavity-and-convexity-containing sheet member, its handling, cost, etc. being taken into account, it is preferred that the projections forming the convex portions are 0.3 mm or greater in height, more preferably 0.5 to 1.5 mm.

It is acceptable either that the concave portions and convex portions are provided on one surface only or that they are provided on both surfaces.

As the material for the concavity-and-convexity-containing sheet member, an aqueous liquid impermeable film made of resin such as PE, PP, PVA, and urethane, and a water-resistant non-woven fabric, such as SMS non-woven and SMMS non-woven can be listed as examples.

In the concavity-and-convexity-containing sheet member, apertures can also be provided in some of or all of the convex portions.

Figure 7:
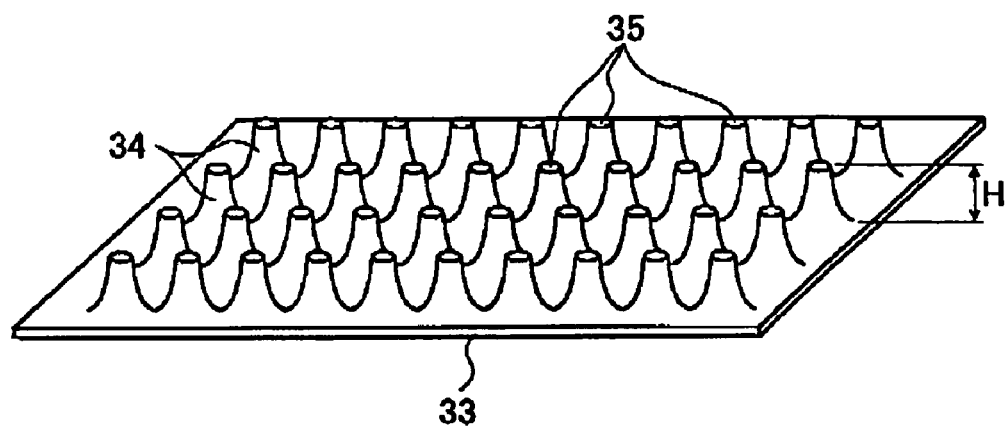
FIG. 7 is an illustrative perspective view of an example of the concavity-and-convexity-containing sheet member that has apertures in all convex portions.

FIG. 7 is an illustrative perspective view of an example of a concavity-and-convexity-containing sheet member that has apertures in all convex portions. The concavity-and-convexity-containing sheet member 33 that has apertures in convex portions as shown in FIG. 7 has a number of projections 34 that form the convex portions, each projection 34 having an aperture 35 at the top of it.

With the concavity-and-convexity-containing sheet member that does not have apertures in convex portions as shown in FIG. 6, only the concave portions function as the channel for the aqueous liquid if it is made of a material impermeable to aqueous liquid; but with the concavity-and-convexity-containing sheet member that has apertures in convex portions as shown in FIG. 7, these apertures also function as the channels for the aqueous liquid even if it is made of an aqueous liquid impermeable material. In other words, the aqueous liquid moves via the apertures from one side of the concavity-and-convexity-containing sheet member to the other side. The use of such concavity-and-convexity-containing sheet member, therefore, is preferably made when it covers a relatively large area of the surface of the first super-absorbent sheet.

The apertures may be provided only in some of the convex portions or in all of the convex portions. Furthermore, though there is no limit in particular to the number of apertures per unit area, 1.0 to 100 apertures/cm$^2$ is preferable.

The concavity-and-convexity-containing sheet member has an advantage that the flow of the aqueous liquid is not disrupted even when some convex portions are deformed during use.

Next, disposition of the concavity-and-convexity-containing sheet member will be explained.

Figure 8:
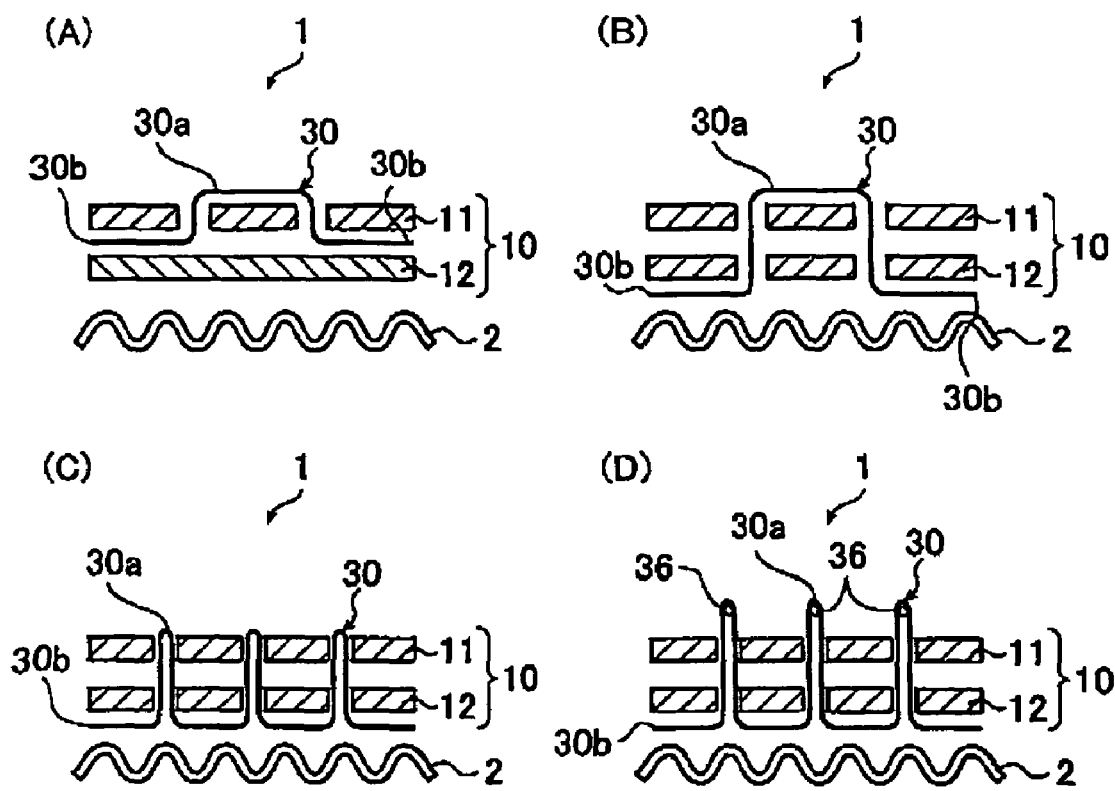
FIG. 8 is a group of explanatory drawings showing examples of the concavity-and-convexity-containing sheet member disposition.

FIG. 8 is a group of explanatory drawings showing examples of the concavity-and-convexity-containing sheet member disposition. In FIG. 8, the absorber 1 of the present invention has a laminated absorbent member 10 composed of two layers of super-absorbent sheets 11 and 12, a concavity-and-convexity-containing sheet member 30, and a back-sheet 2 provided under the super-absorbent sheet 12. FIGS. 8(A) through (D) are the sectional views of examples of the absorber of the present invention.

In each example shown in FIGS. 8(A) through (D), a portion 30a of the concavity-and-convexity-containing sheet member 30 is positioned to be higher than the super-absorbent sheet 11 in such a way that the concavity-and-convexity-containing surface (not shown) faces upward.

In the example shown in FIG. 8(A), a portion 30a of the concavity-and-convexity-containing sheet member 30 is positioned to be higher than the super-absorbent sheet 11 in such a way that it partially covers the super-absorbent sheet 11. Also, other portions 30b of the concavity-and-convexity-containing sheet member 30 are positioned above the super-absorbent sheet 12 (that is, between the first super-absorbent sheet 11 and the super-absorbent sheet 12). Therefore, the aqueous liquid fed to the first super-absorbent sheet 11 is absorbed in the first super-absorbent sheet 11 in part, but the rest moves via the concavity-and-convexity-containing sheet member 30 to the super-absorbent sheet 12 where it is diffused and absorbed entirely on its surface.

In the example shown in FIG. 8(B), a portion 30a of the concavity-and-convexity-containing sheet member 30 is positioned to be higher than the super-absorbent sheet 11, in such a way that it partially covers the super-absorbent sheet 11. Also, the other portions 30b of the concavity-and-convexity-containing sheet member 30 are positioned under the laminated absorbent member 10 (that is, between the super-absorbent sheet 12 which makes the lowermost layer of the laminated absorbent member and the back-sheet 2).

In the example shown in FIG. 8(C), portions 30a of the concavity-and-convexity-containing sheet member 30 are positioned to be higher than the super-absorbent sheet 11 in such a way that they do not cover a part of the super-absorbent sheet 11. Also, other portions 30b of the concavity-and-convexity-containing sheet member 30 are positioned under the laminated absorbent member 10.

In the example shown in FIG. 8(D), portions 30a of the concavity-and-convexity-containing sheet member 30 are positioned to be higher than the super-absorbent sheet 11, in such a way that they do not cover a part of the super-absorbent sheet 11 but rather that they project and stand up. Here, elastics 36, such as polyurethane filaments are inserted inside the portions 30a of the concavity-and-convexity-containing sheet member 30. Also, the other portions 30b of the concavity-and-convexity-containing sheet member 30 are positioned under the laminated absorbent member 10.

In the examples shown in FIGS. 8(B) through (D), therefore, the aqueous liquid fed to the first super-absorbent sheet 11 is absorbed in the first super-absorbent sheet 11 in part, but the rest moves via the concavity-and-convexity-containing sheet member 30 to the bottom surface of the super-absorbent sheet 12 where it is diffused and absorbed entirely on its surface.

(3) Non-woven Sheet Member

In a non-woven sheet member, air gaps inside thereof function as the channel for the aqueous liquid. There is no limit in particular to the non-woven sheet member's shape, size, material, manufacturing method, etc., but one that is bulky and is of high resilience is preferred.

"High resilience" here means, in general, having the characteristics of great compression-resistance, i.e., not getting flattened when a load is applied. It is preferred in particular that it has high resilience and does not get flattened when it is wet (in use).

The preferred material of high resilience used for the non-woven sheet member is a hydrophobic synthetic fiber with a high Young's modulus in a wet environment preferably of 3 d or above or more preferably of coarse denier of 5 to 12 d, or even more preferably a synthetic fiber with crimps. A more specific example is a composite fiber of bi-component polyester, often used for stuffing of bottom futon mats. As bulkiness is expressed as a measure of basis weight and apparent specific gravity, in the present invention, the preferred basis weight is 20 mg/m$^2$ or more and apparent specific gravity 0.1 g/cm$^3$ or less. A bulky non-woven fabric generally used as a temporary retention layer or a so-called "acquisition layer" in absorbent products can also be used.

There is no restriction in particular on the method of manufacturing non-woven fabric by using these fibers; the thermal-bond non-woven (for example, the non-woven fabric composed of a bulky water-impermeable phase of low apparent density, constructed in the form of laminate of the hydrophobic and hydrophilic fiber layers and a water-permeable phase of high apparent density, constructed in the form of the compressed mixture of hydrophobic and hydrophilic fibers, which is suggested by the inventors of the present invention in JP 2002-20957 A) and the non-woven fabric in a multi-layered structure (for example, the composite sheet made by bonding a paper layer or non-woven fabric layer with a flat and smooth surface and the fiber web layer with a bulky and uneven surface alternately with one another, which is suggested by the inventors of the present invention in the specification of Japan Patent Application No. 2001-297161 and the specification of Japan Patent Application No. 2001-297162), for example, are preferred.

Figure 9:
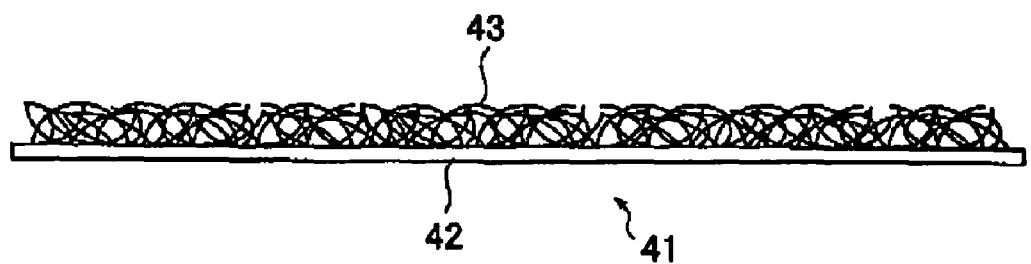
FIG. 9 is an illustrative sectional view showing an example of the non-woven sheet member.

FIG. 9 is an illustrative sectional view showing an example of the non-woven sheet member. The non-woven sheet member 41 shown in FIG. 9 is a bulky non-woven fabric composite of a PP spunbond non-woven fabric 42 and a polyester fiber web 43. A more specific example will be a bulky non-woven fabric of about 1.5 mm thickness, obtainable by compositing with spot-thermal-bonding a PP spunbond non-woven fabric of 13 g/m$^2$ with an average denier of 2.2 d (manufactured by Avgol) and a carded-web (30 g/m$^2$) of the 8 d×61 mm polyester fiber (manufactured by Unitika Ltd.), which is a PE/PET side-by-side composite fiber.

Next, the disposition of the non-woven sheet member will be explained.

The disposition of the non-woven sheet member is the same as that of the above-described disposition of the concavity-and-convexity-containing sheet member, but it will be explained here with the more specific examples.

Figure 10:
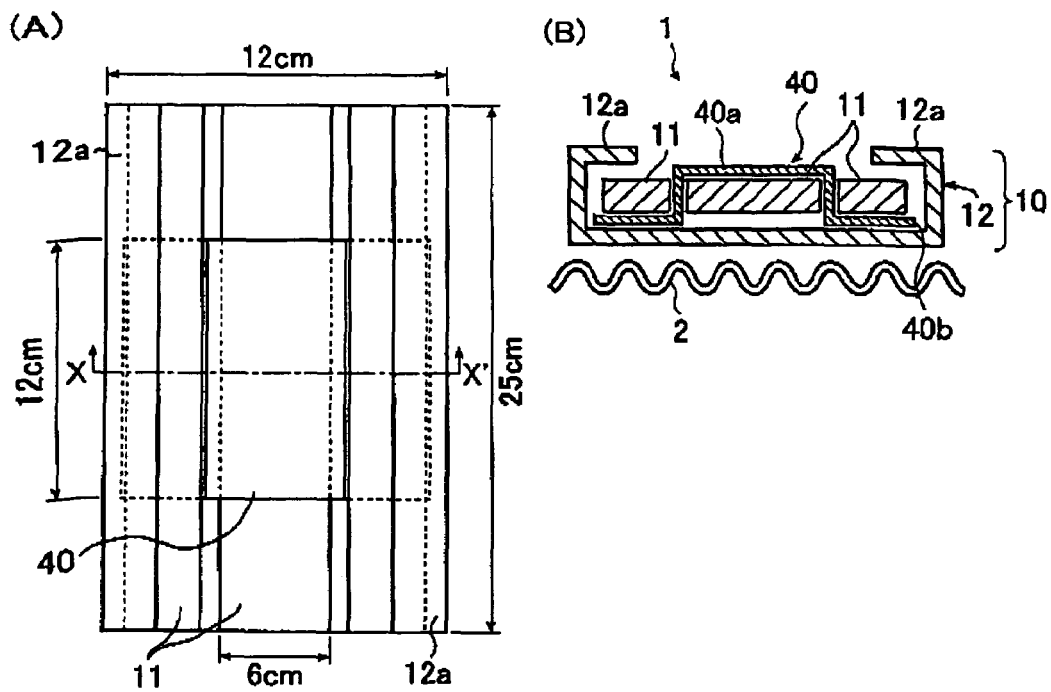
FIG. 10 is a set of explanatory drawings showing an example of the non-woven sheet member disposition.

FIG. 10 is a set of explanatory drawings showing an example of the non-woven sheet member disposition. In FIG. 10, the absorber 1 of the present invention has the laminated absorbent member 10 composed of two layers of super-absorbent sheets 11 and 12, the non-woven sheet member 40, and the back-sheet 2 provided under the super-absorbent sheet 12. FIG. 10(A) is a top view and FIG. 10(B) is a sectional view taken along the line X-X' of FIG. 10(A).

In the example shown in FIG. 10, a portion 40a of the non-woven sheet member 40 is positioned above the super-absorbent sheet 11, in such a way that it partially covers the super-absorbent sheet 11. Also, other portions 40b of the non-woven sheet member 40 are positioned above the super-absorbent sheet 12 (that is, between the first super-absorbent sheet 11 and the super-absorbent sheet 12). Furthermore, the super-absorbent sheet 12 forms a side-guard 12a at each end of the absorber in the direction of X-X', by being folded in such a manner to partially cover both ends of the first super-absorbent sheet 11. Therefore, the aqueous liquid fed to the first super-absorbent sheet 11 is diffused into both the first super-absorbent sheet 11 and the super-absorbent sheet 12 and thus quickly absorbed.

In the absorber of the present invention, covering the area in vicinity of the center portion of the first super-absorbent sheet 11 with a portion 40a of the non-woven sheet member 40 to function as a skin-contact sheet is one of the preferred embodiments.

(4) Hydrophilic Fiber or its Fiber Bundle

In the hydrophilic fiber or its fiber bundle, a channel is formed as the aqueous liquid flows through it by capillary action.

Figure 11:
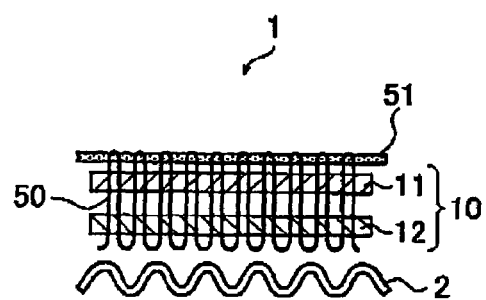
FIG. 11 is a sectional view of an example of the absorber of the present invention, explaining the disposition of the fiber bundle of the hydrophilic fiber.

FIG. 11 is a sectional view of an example of the absorber of the present invention, explaining the disposition of the fiber bundle of the hydrophilic fiber. In FIG. 11, the absorber 1 of the present invention has a laminated absorbent member 10 composed of two layers of super-absorbent sheets 11 and 12, a fiber bundle of the hydrophilic fiber 50, and a back-sheet 2 provided under the super-absorbent sheet 12.

In the example shown in FIG. 11, an acquisition web 51, which is a water-permeable fiber web, is provided over the first super-absorbent sheet 11, and the acquisition web 51, the first super-absorbent sheet 11 and the super-absorbent sheet 12 are sewn up together with the fiber bundle of the hydrophilic fiber 50. A carded web composed of a hydrophilic-treated polyester fiber, for example, may be used as the acquisition web 51.

Note that provision of the acquisition web 51 is not a requirement in the present invention. It will be acceptable as long as the first super-absorbent sheet 11 and its tangent super-absorbent sheet 12 are sewn up together.

The first super-absorbent sheet 11 and the super-absorbent sheet 12 can be sewn up by a needle-punching process, for example.

The explanation so far has been of the preferred by-pass channel members, but the by-pass channel members used in the present invention are not limited to these. It is acceptable as long as it has the channel to move the aqueous liquid, fed to the first super-absorbent sheet positioned at the uppermost part of the laminated absorbent member, from the first super-absorbent sheet to another super-absorbent sheet. In other words, it is acceptable if the by-pass channel member has entries and exits along with channels to link therebetween.

The entries of the by-pass channel may be one aperture or more than one; either is acceptable. The entries of the by-pass channel are most commonly provided on the first super-absorbent sheet, but when there is an acquisition layer or a skin-contacting layer on the first super-absorbent sheet, it is also acceptable to position the entries on them. Furthermore, in case a super-absorbent sheet other than the first super-absorbent sheet is exposed when viewed from the top, it is also acceptable to position the entries on the exposed super-absorbent sheet.

FIGS. 12(A) through (G) are the explanatory drawings, each showing an example of planar distribution of the entries of the by-pass channel members.

Figure 12:
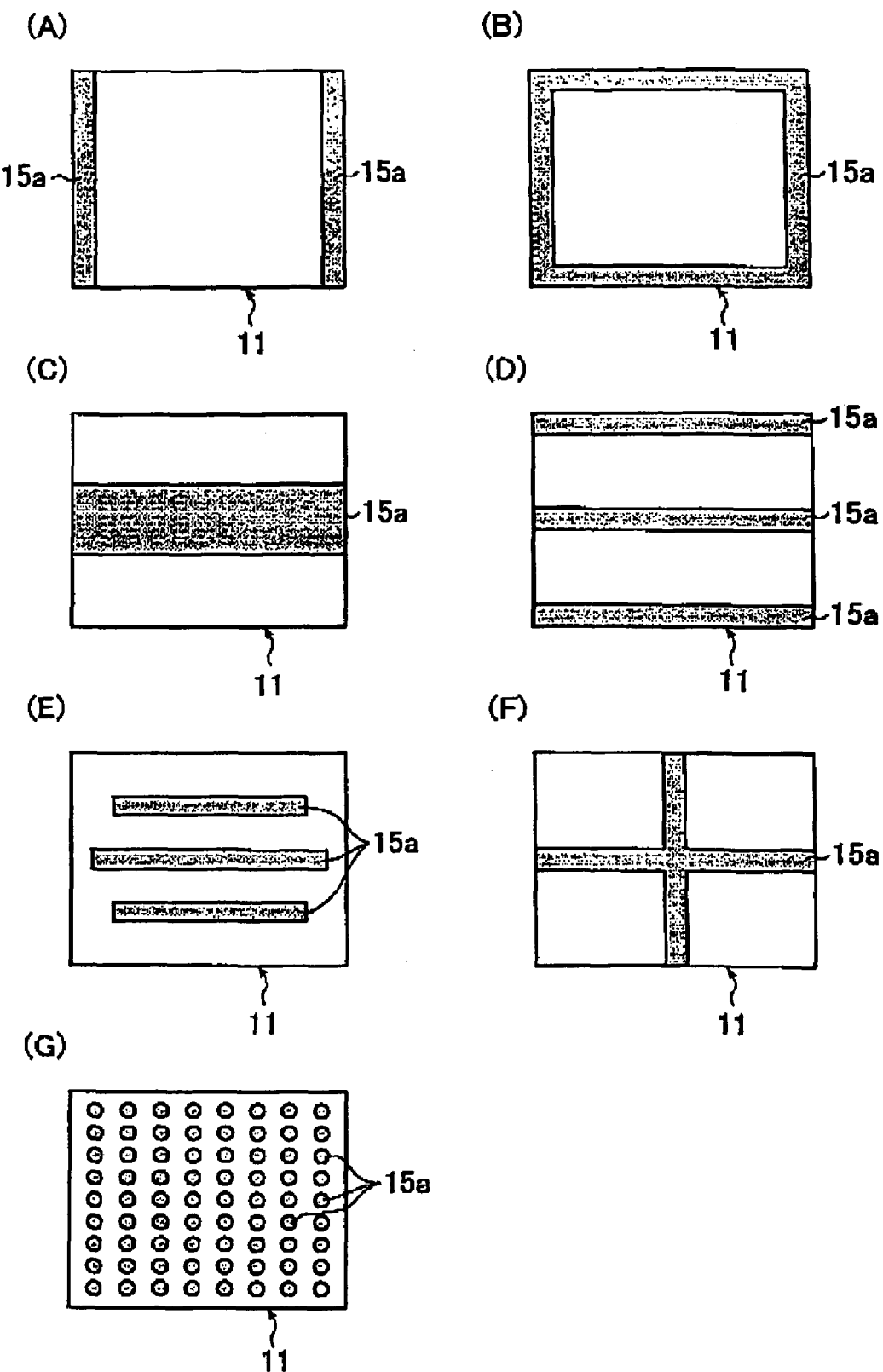
FIGS. 12(A) through (G) are the explanatory drawings, each showing an example of planar distribution of the entries of the by-pass channel members.

In FIG. 12(A), the entries 15a of the by-pass channel member 15 are positioned lengthwise on both ends of the first super-absorbent sheet 11 located at the uppermost part of the laminated absorbent member 10.

In FIG. 12(B), the entry 15a of the by-pass channel member 15 is positioned in the marginal region all around the first super-absorbent sheet 11.

In FIG. 12(C), the entry 15a of the by-pass channel member 15 is positioned, in the form of a relatively wide band, in the center widthwise of the first super-absorbent sheet 11, and extending in a longitudinal direction.

In FIG. 12(D), the entries 15a of the by-pass channel member 15 are positioned, in the form of relatively narrow plural bands (three bands in this example), in the center and at both ends widthwise of the first super-absorbent sheet 11.

In FIG. 12(E), the entries 15a of the by-pass channel member 15 are positioned, in the form of relatively narrow plural bands (three in this example), in the center widthwise of the first super-absorbent sheet 11.

In FIG. 12(F), the entries 15a of the by-pass channel member 15 are positioned, in the form of a cross, in the center widthwise and the center lengthwise of the first super-absorbent sheet 11.

In FIG. 12(G), the entries 15a of the by-pass channel member 15 are positioned, in the form of numerous dots, all over the surface of first super-absorbent sheet 11.

The forms and shapes as well as the planar distribution of entries of the by-pass channel members are not limited to the above; they can be determined according to such factors as the design of the absorber of the present invention and the material used for the by-pass channel members.

The disposition, shapes, forms, etc. of the exits of the by-pass channel members can be determined according to the super-absorbent sheet for moving the aqueous liquid and the disposition of the exits on the super-absorbent sheet.

The absorber of the present invention only has to include at least one by-pass channel member that has the channel to move the aqueous liquid fed to the first super-absorbent sheet from the first super-absorbent sheet to another super-absorbent sheet, and in addition to this, it may also include the by-pass channel member to move the aqueous liquid between other super-absorbent sheets (between the super-absorbent sheet 12 and the super-absorbent sheet 13 in FIG. 2, for example).

The absorber of the present invention can also include a member that allows diffusion, within the same super-absorbent sheet, of the fed-in aqueous liquid.

In the present invention, the by-pass channel member does not have to be an independent member, but instead its function may be fulfilled by a super-absorbent sheet, or a skin-contact sheet, back-sheet, gathers, etc., that are commonly used in absorbent products, taking a different form.

The role of the by-pass channel members described above is to dramatically improve the absorbing speed of the entire absorber, as well as to enable efficient utilization of the entire surface of every layer of the super-absorbent sheets.

In a conventional absorber that uses super-absorbent sheets, if excretion of urine takes place in a recumbent position, for example, urine would be concentrated on one side of the absorber due to gravitation. Similarly, in a procumbent position, urine would be concentrated in the lower side of the absorber (the side away from the wearer's skin); in the supine position, urine would be concentrated in the upper side of the absorber (the side nearer to the wearer's skin); and in the standing position or sitting position, urine would be concentrated in the central region of the absorber. In a conventional absorber, therefore, absorption of urine is carried out locally only at the section where urine is concentrated, so, if it does not have enough absorbing capacity, urine would overflow and eventually leak. At the same time, a large area in the absorber will remain hardly absorbing.

Because the wearer's position when urinating varies regardless of the absorber's structure, for the conventional absorber to be able to fully absorb urine in any possible position, it has been necessary to give enough reserve of absorbing capability to all parts of the absorber, so, inevitably, twice or sometimes four times as much absorbing capability had to be given to the absorber.

In contrast to this, in the absorber of the present invention, because urine that has been fed into one part of the absorber is absorbed after it moves rapidly via the channels of the by-pass channel members to the overall surface of each super-absorbent sheet, and because no blocking is caused, the absorbing capacity of the absorber is fulfilled without any loss, and there is very little possibility of leakage. According to the present invention, therefore, because the mass and surface area of the super-absorbent sheets required for the absorber can be dramatically reduced, an extremely compact absorber with excellent absorbing capacity can be realized.

The absorbent product of the present invention is used to be fed with the aqueous liquid to it from the top; the absorbent product includes the aqueous liquid permeable sheet member, the absorber of the present invention as described above, and the aqueous liquid impermeable sheet member, from the top to the bottom in this order.

For the aqueous liquid permeable sheet member, what is commonly used as a skin-contact sheet can be used. More specifically, PP non-woven, polyolefin-polyester non-woven as well as their cotton blend, for example, can be used.

For the aqueous liquid impermeable sheet member, what is commonly used as the back-sheet can be used. More specifically, a PE film as well as a laminated PE film with PP non-woven thereunder, for example, can be used.

The absorbent product of the present invention only has to have the above structure, and it can also have other members aside from the above, such as inside-gather and outside-gather.

Since using the absorber of the present invention, the absorbent product of the present invention is extremely compact, has excellent absorbing capability and is free from the risk of leakage.

EXAMPLE

Hereinafter, the present invention will be explained in detail by showing an example, but the present invention shall not be limited by this.

The absorber shown in FIG. 10 was made.

For the super-absorbent sheets 11 and 12, the sheets made by coating SAP dispersion slurry on polyester non-woven fabric (MegaThin (Registered Trademark in Japan) manufactured by Japan Absorbent Technology Institute, SAP: 180 g/m$^2$) was used.

For the non-woven sheet member 40, a bulky composite non-woven sheet made of PP spunbond non-woven fabric 42 and polyester fiber web 43 shown in FIG. 9 was used. More specifically, a bulky non-woven sheet of about 1.5 mm thickness was used, which was obtained by compositing with spot-thermal-bonding PP spunbond non-woven fabric of 13 g/m$^2$ with average denier of 2.2 d (manufactured by Avgol) and the carded-web (30 g/m$^2$) of the 8 d×61 mm polyester fiber (manufactured by Unitika Ltd.), which is a PE/PET side-by-side composite fiber.

For the back-sheet 2, the concavity-and-convexity-containing PE film (20 g/m$^2$) manufactured by Tredeger was used.

Other dimensions of each member are shown in FIG. 10(A).

Next, using this absorber 1, absorbency and diffusion were evaluated.

Figure 13:
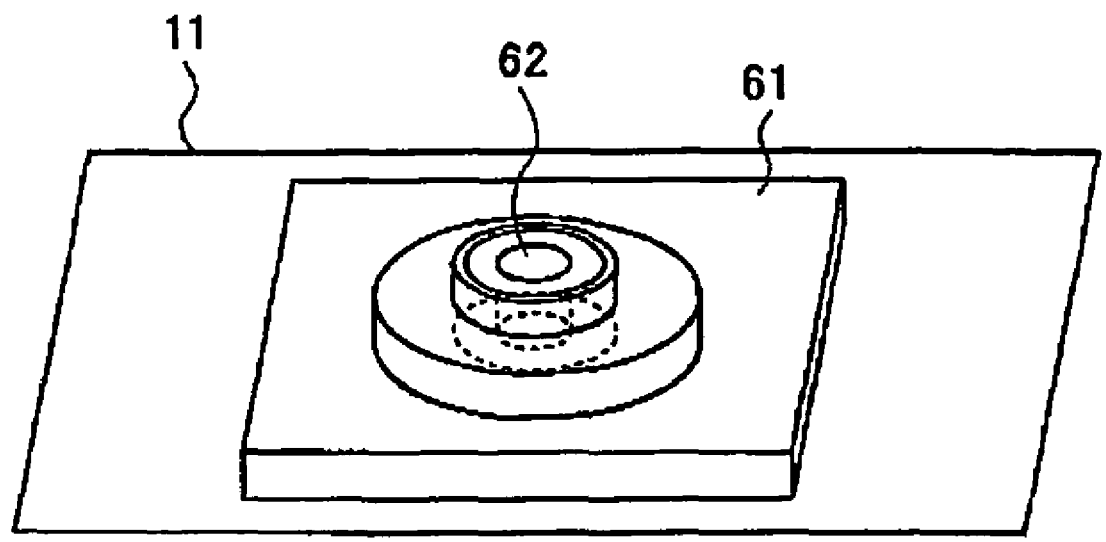
FIG. 13 is an explanatory illustration of an evaluation test of the absorber.

FIG. 13 is an explanatory illustration of an evaluation test of the absorber. In FIG. 13, only the super-absorbent sheet 11 of the absorber 1 is shown, and the rest of the members are omitted.

As shown in FIG. 13, a weight 61 of 0.1 psi (70.3 g/cm$^2$), which has an inlet 62 of 2 cm inside diameter, is placed in the center of the first super-absorbent sheet 11, and 100 mL of saline were added three times, thus, 300 mL in total, from the inlet 62. Intervals between the end of the first addition and the beginning of the second addition and between the end of the second addition and the beginning of the third addition were both 10 minutes.

The absorbing speed and diffusion area were measured at each addition. The absorbing speed was evaluated by measuring the time period from the beginning of each addition to when it was visually confirmed that 100 mL of saline was completely absorbed. The diffusion area was obtained by first taking a photo of the absorber when complete absorption of added 100 mL saline had been visually confirmed, and then measuring on the photo the wetted area resulting from absorbing the saline.

The results are shown in Table 1. An absorber of the exact same structure as that of the absorber 1 of the present invention except for the missing non-woven sheet member 40 was used as a Comparative Example.

TABLE 1

|  | Absorbing Speed (sec/100 mL) | | | Diffusion Area (cm$^2$) | | |
| --- | --- | --- | --- | --- | --- | --- |
|  | 1$^{st}$ | 2$^{nd}$ | 3$^{rd}$ | 1$^{st}$ | 2$^{nd}$ | 3$^{rd}$ |
| Example | 14 | 17 | 15 | 200 | 270 | 300 |
| Comparative Example | 168 | 228 | 345 | 90 | 132 | 145 |

Table 1 indicates a 10 times faster absorbing speed and twofold improvement in the diffusion area of the absorber of the present invention having a by-pass channel member, compared to the absorber of the Comparative Example having no by-pass channel member.

INDUSTRIAL APPLICABILITY

As explained above, the absorber of the present invention realizes a remarkable improvement in the absorbing speed of aqueous liquid and expansion of diffusion area, while maintaining various features required for absorbers, such as flexibility. This was realized by providing in the absorber comprising laminated two or more super-absorbent sheets, the by-pass channel member that has the channel for moving the aqueous liquid fed to the first super-absorbent sheet which is situated at the uppermost part of the laminated absorbent member, from this first super-absorbent sheet to another super-absorbent sheet positioned below. When applied in various absorbent products, the absorber of the present invention is able to exhibit significant positive effects, including ensuring prevention of accidents such as leakage.

The invention claimed is:

1. An absorber comprising:
    a laminated absorbent member comprised of laminated two or more super-absorbent sheets, a first upper super-absorbent sheet of the super-absorbent sheets has an uppermost surface, each of said super-absorbent sheets containing a super-absorbent polymer capable of absorbing aqueous liquid, and
    a by-pass channel member which has a channel for moving aqueous liquid, fed to the uppermost surface of said first super-absorbent sheet, from the uppermost surface of the first super-absorbent sheet to another super-absorbent sheet of the super-absorbent sheets; and
    wherein the by-pass channel member transports a portion of liquid disposed at the uppermost surface of the first super-absorbent sheet to said another super-absorbent sheet so that the portion of the liquid transported by the by-pass channel member to said another super-absorbent sheet is not absorbed by the first super-absorbent sheet, and the first super-absorbent sheet is closer to a skin of a user than the another super-absorbent sheet when the absorber is worn by the user,
    at least a part of the by-pass channel member is composed of a non-woven sheet member, air gaps inside thereof function as the channel for moving the aqueous liquid;
    a part of the non-woven sheet member is positioned above the first super-absorbent sheet; and
    another part of the non-woven sheet member is positioned either above the another super-absorbent sheet or under the laminated absorbent member or both.

2. The absorber according to claim 1, wherein at least one layer of the super-absorbent sheets contains 50 wt % or more of the super-absorbent polymer and a thickness of the super-absorbent sheet is 1.5 mm or less.

3. The absorber according to claim 1, wherein a part of the non-woven sheet member is positioned above the first super-absorbent sheet so as to rise from a surface thereof.

4. The absorber according to claim 1, wherein a part of the non-woven sheet member covers an area in a vicinity of a center portion of the first super-absorbent sheet, and functions as a skin-contact sheet.

5. An absorbent product to be fed with an aqueous liquid from an upper side thereof, comprising an aqueous liquid permeable sheet member, the absorber according to claim 1, and an aqueous liquid impermeable sheet member, from the top in this order.

6. An absorber of claim 1, wherein the by-pass channel member also transports a portion of the aqueous liquid fed directly onto the by-pass channel member to said another super-absorbent sheet.

7. The absorber according to claim 1, wherein the basis weight of the non-woven sheet member is 20 mg/m$^2$ or more.

8. The absorber according to claim 1, wherein apparent specific gravity of the non-woven sheet member is 0.1 g/cm$^3$ or less.

9. The absorber according to claim 1, wherein the non-woven sheet member uses thermal-bond non-woven fabric.

10. The absorber according to claim 9, wherein the thermal-bond non-woven fabric is constructed in the form of laminate of the hydrophobic and hydrophilic fiber layers.

11. The absorber according to claim 1, wherein the non-woven sheet member uses non-woven fabric in a multi-layered structure.

12. The absorber according to claim 11, wherein the non-woven fabric in a multi-layered structure is a composite sheet made by bonding a paper layer or non-woven fabric layer with a flat and smooth surface altenately with one another.

* * * * *